US00PP12352P2

(12) United States Plant Patent
Walden

(10) Patent No.: US PP12,352 P2
(45) Date of Patent: Jan. 15, 2002

(54) MINIATURE ROSE PLANT NAMED 'JACHOTTA'

(75) Inventor: John K. Walden, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/427,571

(22) Filed: Oct. 26, 1999

(51) Int. Cl.[7] ..... A01H 5/00
(52) U.S. Cl. ..... Plt./121
(58) Field of Search ..... Plt./121, 122, 128, Plt./129

*Primary Examiner*—Howard J. Locker
(74) *Attorney, Agent, or Firm*—Klarquist Sparkman, LLP

(57) ABSTRACT

A miniature rose plant having the unique combination of a compact, rounded growth habit; bright, deep pink colored, distinctive, small hybrid tea-shaped flowers; and small, dark green, disease resistant foliage.

1 Drawing Sheet

Figure 8:
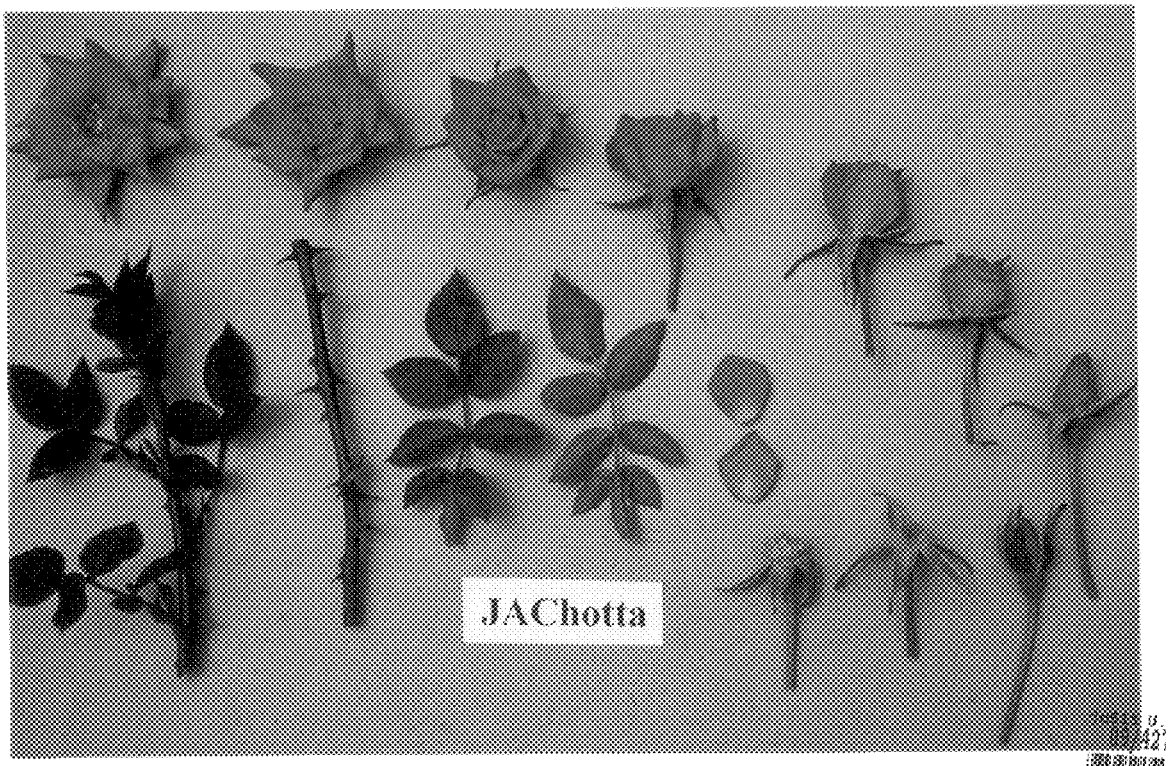

The present invention relates to a new and distinct variety of rose plant of the miniature class which was originated by me by discovering in May 1998 in rose production fields in Wasco, Calif., a novel flower color mutation on a single branch of the variety JACpoy (U.S. Plant Pat. No. 9,015).

'JAChotta' distinguishes from its parent in its deep pink flowers as compared to the yellow and orange flowers of JACpoy. It has the compact (dwarf) growth habit, hybrid tea-shaped blooms, and small, dark green, disease resistant foliage of its parent.

Asexual reproduction of this new variety by cutting, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Parent.*—Spontaneous mutant of JACpoy (U.S. Plant Pat. No. 9,015).

Classification:

*Botanical.*—*Rosa hybrida.*

*Commercial.*—Miniature rose.

FLOWER

Observations made from specimens grown in a garden environment at Somis and Wasco, Calif. from September 1992 through August 1999.

Blooming habit: Recurrent.

Bud:

*Size.*—⅝ to ¾ inch long when the petals start to unfurl.

*Form.*—The bud form is short; pointed ovoid.

*Color.*—When sepals first divide, bud color is near Red Group 53B. When half blown, the upper sides of the petals are Red Group 51A, with a ¼ inch yellow (near Yellow Group 7D) crescent on the lower ⅓ of the petal; and the lower sides of the petals are Red Group 52B, with a ¼ inch yellow (near yellow Group 7D) crescent on the lower ⅓ of the petal.

*Sepals.*—Color; Yellow-Green Group 144B. Surface texture: Rough; glandular and hairy. There are three lightly appendaged sepals. There are two unappendaged sepals with hairy edges.

*Receptacle.*—Color: Yellow-Green Group 144A. Shape: Funnel. Size: Small (about ¼ inch×¼ inch). Surface: Hairy.

*Peduncle.*—Length: Short (about 1⅝ inches). Surface: Rough; glandular. Color: Yellow-Green Group 144A. Under bright light an anthrocyanin blush of Greyed-Purple Group 183D may be visible.

Bloom:

*Size.*—Small. Average open size is 2¼ inches.

*Borne.*—Singly and several together in rounded clusters of three to seven blooms.

*Stems.*—Strength: Strong. Average length is about six to eight inches.

*Form.*—When first open: High centered. Permanence: Retains its form to the end; outer petal edges curl slightly.

*Petalage.*—Number of petals under normal conditions: 30–35.

*Color.*—The upper sides of the petals are Red Group 51A with a Yellow Group 7D crescent on the lower ⅓ of the petal. The reverse sides of the petals are Red Group 52B with a Yellow Group 7D crescent on the lower ⅓ of the petal. The base of each petal has a Yellow Group 7D colored point of attachment. The major color on the upper side is Red Group 51A.

*Variegations.*—None.

*Discoloration.*—The general tonality at the end of the first day: Unchanged. At the end of the third day: Slight loss of intensity, otherwise still Red Group 51A. Before petals drop, color changes to Red Group 54A, the petal base changes to White Group 155D, and this color extends about halfway up the length of the petal. Flower life from bud crack to petal drop is seven to eight days.

*Fragrance.*—Very slight; sweet.

Petals:

*Texture.*—Thick.

*Shape.*—Deltoid.

*Form.*—Tips slightly recurved and moderately quilled.

*Arrangement.*—Imbricated. Petaloids in the center: Few (none to three).

*Persistence.*—Petals drop off cleanly before drying.

*Lastingness.*—On the plant: Fair (about five to six days). As a cut flower: Not tested.

Reproductive parts:

*Anthers.*—Size: Medium. Quantity: Many. Color: Yellow-Orange Group 15C. Arrangement: Regular around styles.

*Filaments.*—Color: Yellow Group 12C.

*Pollen.*—Color: Yellow-Orange Group 15C.

*Styles.*—Color: Near Red Group 43A.

*Stigmas.*—Color: Near Green-White Group 157C.

Plant:

*Form.*—Bush.

*Growth.*—Vigorous; dwarf; upright; branching. At maturity, height is 16–22 inches, width is 18–22 inches.

Foliage: Number of leaflets on normal mid-stem leaves: Five or seven.

*Size.*—Small (3 to 3½ inches long×2 to 2¼ inches wide).

*Quantity.*—Abundant.

*Color.*—New foliage: Upper and lower surfaces: Greyed-Purple Group 183A. Old foliage: Upper surface: Green Group 139A. Lower surface: Yellow-Green Group 147B.

Leaflets:

*Shape.*—Pointed oval.

*Texture.*—Leathery.

*Edge.*—Serrated.

*Serration.*—Double and single.

*Petiole rachis.*—Color: Between Green Group 137 A and Green Group 137B.

*Petiole underside.*—Smooth; occasionally with small prickles.

*Stipules.*—About ⅜ to 7/16 inch long; lightly bearded.

*Disease resistance.*—Resistant to mildew and rust; susceptible to blackspot under normal growing conditions.

Wood:

*New wood.*—Color: Greyed-Purple Group 183A, rapidly turning green. Bark: Smooth.

*Old wood.*—Color: Near Green Group 138A. Bark: Smooth.

Prickles:

*Quantity.*—On main canes from base: Ordinary. On laterals from main canes: Ordinary.

*Form.*—Short (¼ to 3/16 inches long); hooked downward.

*Color when young.*—Near Greyed-Red Group 178B.

*Color when mature.*—Near Grey-Brown Group 199B.

Small prickles:

*Quantity.*—On main stalks: None. On laterals: None.

I claim:

1. A new and distinct variety of rose plant of the miniature class, substantially as herein shown and described, characterized particularly by the unique combination of its compact rounded growth habit; bright deep pink colored, distinctive, small hybrid tea-shaped flowers; and its small, dark green, disease resistant foliage.

* * * * *

UNITED STATES PATENT AND TRADEMARK OFFICE

CERTIFICATE OF CORRECTION

PATENT NO. : PP 12,352 P2
DATED : January 15, 2002
INVENTOR(S) : John K. Walden

It is certified that error appears in the above-identified patent and that said Letters Patent is hereby corrected as shown below:

Column 2,
Line 16, after "may be visible." add -- Strength: Stiff; erect; slender. --.

Signed and Sealed this

Twelfth Day of November, 2002

*Attest:*

*Attesting Officer*

JAMES E. ROGAN
*Director of the United States Patent and Trademark Office*